United States Patent
Pevere et al.

(10) Patent No.: US 6,235,942 B1
(45) Date of Patent: *May 22, 2001

(54) PROCESS FOR PREPARING DIKETONE COMPOUNDS

(75) Inventors: Virginie Pevere; Alain Gadras, both of Lyons (FR); Susan Mary Cramp; Charles Walter Ellwood, both of Ongar (GB)

(73) Assignee: Rhone-Poulenc Agrochimie, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,372

(22) PCT Filed: Jan. 28, 1997

(86) PCT No.: PCT/EP97/00370

§ 371 Date: Oct. 28, 1998

§ 102(e) Date: Oct. 28, 1998

(87) PCT Pub. No.: WO97/28122

PCT Pub. Date: Aug. 7, 1997

(30) Foreign Application Priority Data

Feb. 1, 1996 (EP) .................................................. 96300718

(51) Int. Cl.$^7$ ................................................ C07C 319/14

(52) U.S. Cl. ................................................ 568/42; 568/43

(58) Field of Search ................................ 568/38, 41, 42, 568/43

(56) References Cited

U.S. PATENT DOCUMENTS

| | | | |
|---|---|---|---|
| 2,763,692 | * 9/1956 | Gregory | 568/31 |
| 3,882,104 | 5/1975 | Grisar et al. | 260/240 |
| 3,954,871 | * 5/1976 | Buu-Hoi | 564/363 |
| 4,482,745 | 11/1984 | Maulding | 568/314 |
| 4,670,445 | * 6/1987 | Spitzer | 514/300 |
| 5,015,777 | * 5/1991 | Chisolm | 568/314 |
| 5,334,753 | 8/1994 | Bennetau et al. | 562/405 |
| 5,344,992 | * 9/1994 | Drewes | 568/314 |
| 5,366,957 | 11/1994 | Cain et al. | 504/271 |
| 5,371,064 | 12/1994 | Cramp et al. | 504/271 |
| 5,656,573 | 8/1997 | Roberts et al. | 504/271 |
| 2451566 | 5/1975 | (DE) . | |
| 3836161 | 4/1990 | (DE) . | |
| 195247 | * 9/1968 | (EP) . | |
| 0154494 | 9/1985 | (EP) . | |
| 0195247 | 9/1986 | (EP) . | |

FOREIGN PATENT DOCUMENTS

| | | |
|---|---|---|
| 2047028 | 4/1971 | (DE) . |
| 2418480 | 11/1974 | (DE) . |
| 2441498 | 3/1975 | (DE) . |

(List continued on next page.)

OTHER PUBLICATIONS

CA:85:105335 abs of J Agric Food Chem by Henrick 24(5) pp 1023–9, 1976.*
March's "Advanced Organic Chemistry" p 368, 1968.*
Aliev et al, *Sulfur Lett.*, vol. 12, No. 3, pp. 123–132 (1991).
Crow et al, *Aust. J. Chem.*, vol. 32, No. 1, pp. 123–131 (1979).
Comins et al, *Tetrahedron Lett.*, vol. 24, No. 49, pp. 5465–5468 (1983).
Ruwet et al, *Bull Soc. Chim. Belg.*, vol. 78, No. 9–10, pp. 571–582 (1969).
Buu–Hoi et al, *Chimie Therapeutique*, vol. 2, No. 1, pp. 39–48 (1967).
Sharghi et al, *J. Chem. Eng. Data*, vol. 8, No. 2, pp. 276–278 (1963).
*Chemical Abstracts*, vol. 90, No. 3, Abstract No. 22614p (1979).
Julia et al, *Tetrahedron*, vol. 47, No. 34, pp. 6939–6950 (1991).
*Chemical Abstracts*, vol. 112, No. 1, abstract No. 7509n (1990).

Primary Examiner—Jean F. Vollano
(74) Attorney, Agent, or Firm—Burns, Doane, Swecker & Mathis, L.L.P.

(57) ABSTRACT

A process for preparing compounds of the formula:

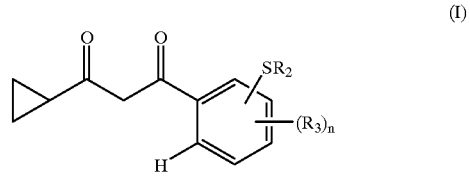

(I)

wherein $R_2$ is lower alkyl; or phenyl optionally substituted by from one to five groups, the same or different, which are lower alkyl, lower haloalkyl, halogen or —$SR_4$; $R_3$ is halogen, lower alkyl, lower haloalkyl, lower alkoxy, lower haloalkoxy, —S-alkyl, cycloalkyl having from 3 to 7 carbon atoms in the ring, alkenyl or alkynyl having from 3 to 7 carbon atoms, or -$(CR_5R_6)_q$—$SR_2$ wherein q is one or two; $R_4$ is lower alkyl; $R_5$ and $R_6$ independently represent hydrogen, lower alkyl or lower haloalkyl; and n is zero or an integer from one to three; intermediate compounds of the formula:

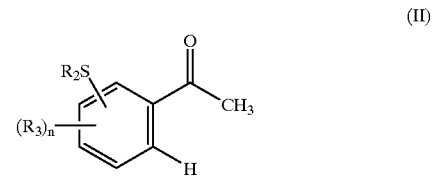

(II)

and processes for preparing them.

7 Claims, No Drawings

FOREIGN PATENT DOCUMENTS

| | | |
|---|---|---|
| 0418175 | 3/1991 | (EP) . |
| 0487357 | 5/1992 | (EP) . |
| 0507013 | 10/1992 | (EP) . |
| 0524018 | 1/1993 | (EP) . |
| 0527036 | 2/1993 | (EP) . |
| 0560482 | 9/1993 | (EP) . |
| 560482 * | 9/1993 | (EP) . |
| 0580439 | 1/1994 | (EP) . |
| 0609798 | 8/1994 | (EP) . |
| 1321701 | 6/1973 | (GB) . |
| 1435639 | 5/1976 | (GB) . |
| 1475890 | 6/1977 | (GB) . |
| 93/13060 | 7/1993 | (WO) . |
| 94/18179 | 8/1994 | (WO) . |

* cited by examiner

PROCESS FOR PREPARING DIKETONE COMPOUNDS

This application is the natural phase of PCT/EP97/009370, filed Jan. 28, 1997 now WO97/28122.

This invention relates to a process for preparing ketone compounds and the products obtained by this process. More particularly the invention relates to the preparation of intermediate compounds in the manufacture of pesticides.

Pesticidal 4-benzoylisoxazoles, particularly 5-cyclopropylisoxazole herbicides and intermediate compounds in their synthesis, are described in the literature, for example in European Patent Publication Nos. 0418175, 0487357, 0527036, 0560482, 0609798 and 0682659.

Various methods for preparing these compounds are known. It is an object of the present invention to provide improved methods for the preparation of these compounds and the intermediate compounds X thereto.

According to one aspect of the invention there is provided a process for the preparation of a compound of formula (I) by the reaction of a compound of formula (II) with a compound of formula (III), according to the reaction scheme Sc1 indicated below:

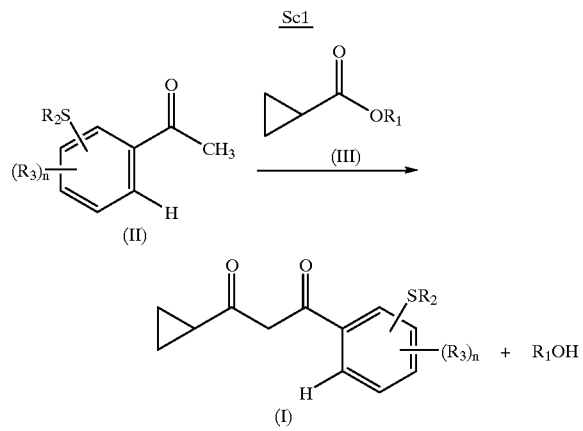

wherein $R_1$ is lower alkyl;

$R_2$ is lower alkyl; or phenyl optionally substituted by from one to five groups which may be the same or different selected from lower alkyl, lower haloalkyl, halogen and —$SR_4$;

$R_3$ is halogen, lower alkyl, lower haloalkyl, lower alkoxy, lower haloalkoxy, —S-alkyl, cycloalkyl having from 3 to 7 ring carbon atoms, alkenyl or alkynyl having from 3 to 7 carbon atoms, or -$(CR_5R_6)_q$—$SR_2$ wherein q is one or two;

n is zero or an integer from one to three;

$R_4$ is lower alkyl;

and $R_5$ and $R_6$ independently represent hydrogen, lower alkyl or lower haloalkyl.

The compounds of formula (I) and a number of processes for their preparation have been described in the European Patent Applications cited above.

By the term "lower" is meant radicals comprising at least one hydrocarbon chain, it being understood that such radicals contain from one to six carbon atoms linked together in a straight- or branched-carbon chain Preferably $R_1$ and $R_2$ are lower alkyl (most preferably methyl).

Preferably the group —$SR_2$ occupies the 2-, 3- or 4-position of the phenyl ring (most preferably the 2-position).

Preferably n is one or two.

The reaction generally proceeds in better yield when a group $R_3$ is not halogen in the 2-position of the phenyl ring. preferably $R_3$ is halogen or trifluoromethyl. More preferably $(R_3)_n$ is 4-$CF_3$ or 3,4-dichloro.

The compounds of formula (III) above are known in the literature and their preparation has been expressly described in the prior art known to the skilled worker. Some references particularly pertinent to the preparation of this reagent may be found by the skilled worker in various sources of chemical literature. including Chemical Abstracts and information databases available to the public.

The preparation of compounds of formula (I) using compounds of formula (II) and (III) according to scheme Sc1 above may be preferably affected in apolar or apolar aprotic solvent Examples of polar aprotic solvents include dimethyl sulphoxide, dimethyl formamide, N,N-dimethylacetamide, N-methyl pyrrolidone, a compound of formula (III); an ether compound, particularly dioxane and tetrahydrofiia; or an aromatic or aliphatic halogenated hydrocarbon, particularly chlorobenzenes. Examples of apolar aprotic solvents include aromatic or aliphatic hydrocarbons, particularly toluene and xylenes.

Generally the reaction temperature used in Sc1above is from 0° C. to the boiling point of the solvent, preferably between 0° C. and 100° C.

Generally the reaction takes place in the presence of a strong base which is most preferably selected from an alkoxide of an alkali or alkaline earth metal, notably sodium ethoxide, sodium methoxide, sodium or potassium t-butoxide; and a metal hydride (notably sodium-hydride).

According to a preferred variant of the process of the present invention the reaction is performed with continuous distillation of the alcohol $R_1$—OH formed in the course of the reaction. at atmospheric pressure or under reduced pressure (preferably from 1 to 20% below atmospheric pressure). Optionally the alcohol $R_1$—OH formed may be removed by the use of a suitable molecular sieve for example 4 Angstrom molecular sieve.

According to a further aspect of the present invention there is provided a process for the preparation of a compound of formula (II) by the reaction of a compound of formula (V) with a mercaptan of formula (IV), optionally present in the form of the thiolate, according to reaction scheme Sc2 indicated below:

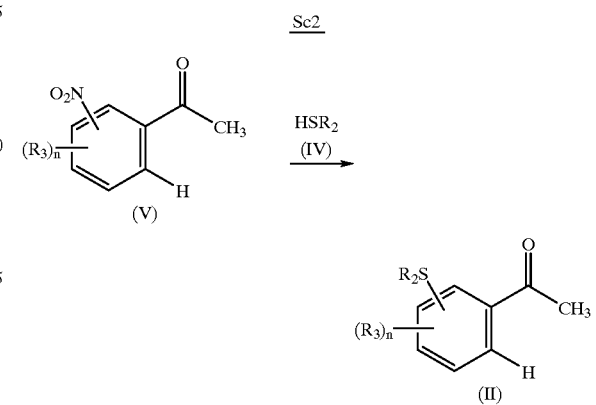

wherein $R_2$, $R_3$ and n in formulae (II) and (V) have the same meanings as given before in reaction scheme Sc1. The group —$NO_2$, is generally present in the 2- or 4-position, preferably the 2-position of the phenyl ring.

Compounds of formula $HSR_2$ are known in the literature and their preparations are expressly described in the prior art known to the skilled worker. The references particularly pertinent to the preparation of this reagent may be found by the skilled worker in various sources of classical chemistry including Chemical Abstracts and information databaes available to the public. The salts or thiolates derived from the compound of formula (IV) may be prepared by means known to the skilled worker. These thiolates are preferably alkine salts, particularly sodium or potassium thiolate.

The preparation of compounds of formula (II) according to scheme Sc2 from the acetophenone of formula (V) and a compound of formula (IV) is preferably performed in a solvent of the compound of formula (IV) which may be inert to the reaction conditions. Examples of other suitable solvents include sulphoxides such as dimetbyl sulphoxide; amides such as dimethyl formamide. N,N-dimethylacetamide and N-methyl pyrrolidone; ketones such as acetone and methyl isobutyl ketone; ether solvents, particularly dioxane and tetmhydroflran; aromatic, aliphatic and cycloaliphatic hydrocarbons and halogenated or non-halogenated hydrocarbons, particularly chlorobenzene, dichloromethane and toluene. The presence of a small quantity of water is also acceptable in allowing the solubilization of the thiolate.

When the reaction according to scheme Sc2 takes place using a compound of formula (IV) in the form of the mercaptan and not in the form of a thiolate salt, the reaction is preferably affected in the presence of a base such as a hydroxide of an alkali metal or alkali earth metal (preferably sodium or potassium), or a carbonate or hydride (such as sodium hydride). The reaction may also be performed using various forms of catalyst, particularly phase transfer catalysts such as a quaternary ammonium salt for example tetrabutylammonium bromide.

According to a further aspect of the invention there is provided a process for the preparation of a compound of formula (V) by the reaction of a compound of formula (VII) or (VI) as well as a process for the preparation of a compound of formula (VI) from a compound of formula (VI), according to the reaction scheme Sc3 indicated below:

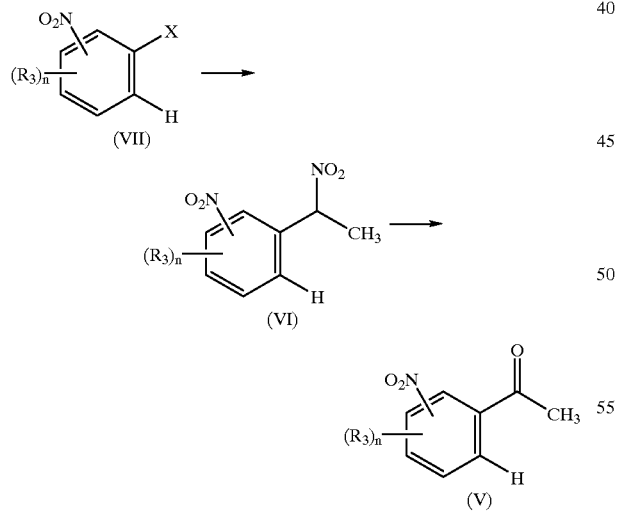

wherein $R_3$ and n have the same meanings as in reaction schemes Sc2 and Sc1, and X represents halogen, preferably chlorine or fluorine. Preferably the group —$NO_2$ in formula (VII) is in the 2- or 4-position, most preferably in the 2-position of the phenyl ring.

These two reactions comprise together the reaction scheme Sc3 above and are generally distinct but preferably they may occur in succession That is, the compounds of formula (V) may be prepared from the compounds of formula (VII) via an intermediate of formula (VI) which may be isolated or used in situ in the course of the reaction.

The reaction conditions for the preparation of the compound of formula (V) from the compound of formula (VI) is known in the art and described in the literature. notably by J. G. Reid and J. M. Reny Runge in Tetrahedron Letters, Vol.31 (1990) pp 1093–1096; G. A. Olah et al, Synthesis (1980) pp 662–663; N. Komblum et al, J.Org.Chem., Vol.47 (1982) pp 4534–38; S.Chandrasekaran et al, Synthetic Communications, Vol.17 (19807) pp 195–201.

The invention is thus also concerned with the preparation of compounds of formula (VI) from compounds of formula (VII) by the reaction of nitroethane in the presence of a base in a solvent which is selected from a compound of formula (VII), nitroethane, a solvent inert to the reaction conditions, and the base being selected from an hydroxide, a carbonate, a hydride, an alkoxide of an alkaline metal or an alkaline earth metal, and guanidine. An advantage of this aspect of the present invention is that relatively simple bases may be used in the reaction scheme Sc3.

Solvents suitable for use include nitroethane itself (used in excess compared to the quantity normally used as a reactant); aromatic or aliphatic halogenated or non-halogenated hydrocarbons, particularly chlorobenzene; aromatic or aliphatic hydrocarbons, particularly toluene and xylenes; polar aprotic solvents such as dimethyl sulphoxide, dimethyl formamide. N,N-dimethylacetamide, N-methyl pyrrolidone; acetonitrile; ether solvents, particularly dioxane and tetrahydrofuran. The presence of a small quantity of water is also acceptable in allowing the solubilization of the reaction mixture, while not reacting with the reactants themselves.

The reaction temperature is generally from 0° C. to 50° C. The reaction may also be carried out in an aqueous or non-aqueous medium. Among the bases suitable for the use in this process one may cite hydroxides or carbonates of alkali metals or alkaline earth metals preferably sodium or potassium, sodium carbonate, potassium carbonate or caesium carbonate; or tetramethylguanidine. These bases may be used alone or in mixture with others. The reaction may also be conveniently performed using various types of catalyst, particularly phase transfer catalysts such as a quartenmy ammonium salt, for example tetrabutylammonium bromide.

Certain intermediate compounds of formula (II) are novel and as such constitute a further feature of the present invention. in particular 2-methylthio-4-ftrifluoromethylacetophenone and 3,4-dichloro-2 (methylthio)acetophenone.

The following non-limiting examples illustrate the invention

EXAMPLE 1

Preparation of 1-cyclopropyl-3-(2-methylthio-4-trifluoromethylphenyl)propne-1,3-dione (reaction scheme Sc1)

In reaction vessel under an inert atmosphere one adds 1.15 g of sodium methoxide and 22 ml of toluene. This is heated to 80° C. at a pressure of 400 mbars. A mixture of 3.3 ml of methyl cyclopropylcarboxylate and 3.8 g of 2-methylthio-4 ftrifluoromethylacetophenone in 6 ml of anhydrous toluene is added ov 3 hours with constant distillation of methanol formed. The reaction is stirred for one hour at 80° C. The reaction is then cooled and the diketone precipitated in a mixture of 80 ml of ice water containing 0.75 ml of concentrated sulphuric acid. The organic phase is retained, washed with water and the toluene removed under reduced pressure to give 3.67 g of 1-cyclopropyl-3-(2-methylthio-4 trifluoromethylphenyl)propane-1,3-dione in the form of an or powder, m.p. 64° C. Yield=75%.

By proceeding in a similar manner way heating at a temperature of 70° C. and a pressure of 230 mbars) 3-(4-chloro-2-methylthiophenyl)-1cyclopropylpropan-1,3-dione was prepared in 98% yield (purity greater than 80%). This compound was also similarly prepared wherein the reaction took place at a temperate of 700 for 6.5 hours and in the presence of 4 Angstrom molecular sieves in place of constant distillation of the methanol formed.

EXAMPLE 2

Preparation of 1-clopropyl-3-[3,4-dichloro-2-(methylthio)phenyl]propane-1,3-dione (reaction scheme Sc1).

Sodium hydride (0.178 g, 60% oil dispersion. 0.0045 M) is suspended in tetrahydrofuran(1.8 ml), stirred and heated at reflux while a solution of a mixture of methyl cyclopropanecarboxylate (0.42 g, 0.0042M) and 3,4-dichloro-2-(methylthio)acetophenone (0.5 g, 0.0021M) in tetmhydrofian (3 ml) is added. The mixture is sired and heated at reflux for 3.5 hours then cooled and poured onto saturated aqueous sodium bicarbonate. The mixture is then extracted with ether, washed with brine, dried over magnesium sulphate, filtered and evaporated to give a gum which is purified by dry column flash chromatography eluted with ethyl acetate in cyclohexane to give 3-cyclopropyl-1-[3,4-dichloro-2-(methylthio)phenyl]propane-1,3-dione (0.35 g, 55%) as a yellow oil.

EXAMPLE 3

Preparation of 2-methylthio-4-ftrifluoromethylacetophenone (reaction scheme Sc2)

To 0.15 of 2-nitro-4-trifluoromethvlacetophenone diluted in 0.5 ml of acetone is added 0.256 g of an aqueous solution of 21% wt/wt sodium thiomethoxide and the mixture is stirred for five hours at 20° C. The aqueous phase is separated then removed, 2 ml of water are added and the acetone removed under reduced pressure. The mixture is then treated with dichloromethane and the aqueous phase removed. The organic phase is washed with fresh water then the solvent is evaporated under reduce pressure to obtain 0.085 g of 2-methylthio 4-trifluoromethylacetophenone with a melting point of 71° C.

By proceeding in a similar manner 3,4-dichloro2-(methylthio)acetophenone may be prepared, $^1$H NMR (CDCl$_3$) 2.4(s,3H), 2.6(s,3H), 7.15(d,1H), 7.5 (d,1H).

EXAMPLE 4

Preparation of 1-(2-nitro-4-trifluoromethylphenyl)-1-nitroethane (Reaction Scheme Sc3).

0.87 g of sodium carbonate in 5 ml of anhydrous toluene are placed in a 30 ml reaction vessel, and 0.11 g of benzyltnethylamronium chloride and 1.13 g of 4-chloro-3-nitro-benzotifluoride and 0.38 g of nitroedhame are added at the same time. The mix is sired for 16 hours at 20° C., 10 ml of water is added and the aqueous phase is separated then acidified by a 4N solution of sulphuric acid. It is then extracted with 5 ml of methyl t-butyl ether. After removing the organic solvent 0.18 g of a mixture is obtained which is separated by column chromatography using reverse phase silica eluting with a mixture of water and acetonitrile to obtain 0.12 g of the title compound, m.p. 48° C.

What is claimed is:

1. A process for the preparation of a compound of formula (I) by reacting a compound of formula (II) with a compound of formula (III), according to the reaction scheme indicated below:

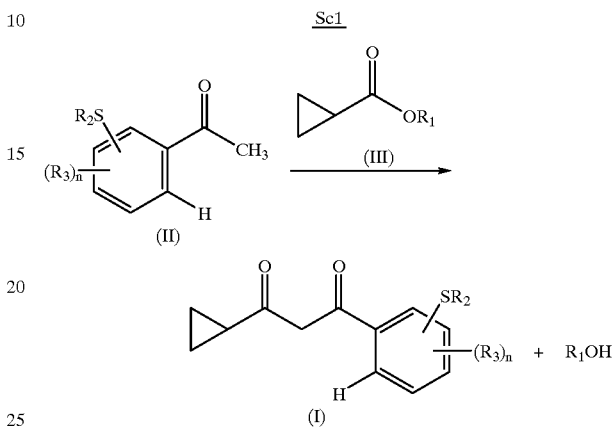

wherein:

$R_1$ is lower alkyl;

$R_2$ is lower alkyl; or phenyl which is unsubstituted or is substituted by from one to five groups which are the same or different selected from the group consisting of lower alkyl, lower haloalkyl, halogen and —$SR_4$;

$R_3$ is halogen, lower alkyl, lower haloalkyl, lower alkoxy, lower haloalkoxy, —S-alkyl, cycloalkyl having from 3 to 7 carbon atoms in the ring, alkenyl or alkynyl having from 3 to 7 carbon atoms, or -$(CR_5R_6)_q$—$_{SR2}$ wherein q is one or two;

$R_4$ is lower alkyl;

$R_5$ and $R_6$ independently represent hydrogen, lower alkyl or lower haloalkyl;

and n is zero or an integer from one to three;

wherein the reaction is performed in an aprotic solvent, in the presence of a strong base, with continuous distillation of the alcohol $R_1$—OH formed in the course of the reaction, at atmospheric pressure or under reduced pressure.

2. A process according to claim 1 wherein the reaction is performed at a temperature of from 0° C. to the boiling point of the solvent.

3. A process according to claim 2, performed at a temperature between 0° C. and 100° C.

4. A process according to claim 1, wherein the strong base is an alkoxide of an alkali or alkaline earth metal or a metal hydride.

5. A process according to claim 2, wherein the strong base is an alkoxide of an alkali or alkaline earth metal or a metal hydride.

6. A process according to claim 1, wherein the reaction is performed at from 1 to 20% below atmospheric pressure.

7. A process according to claim 2, wherein the reaction is performed at from 1 to 20% below atmospheric pressure.

* * * * *